United States Patent [19]
Fabry et al.

[11] Patent Number: 5,117,032
[45] Date of Patent: May 26, 1992

[54] PROCESS FOR MAKING GLYCEROL ETHER SULFATES

[75] Inventors: Bernd Fabry, Korschenbroich; Bert Gruber, Bedburg, both of Fed. Rep. of Germany; James R. Tucker, Cincinnati, Ohio; Brigitte Giesen, Düsseldorf, Fed. Rep. of Germany

[73] Assignee: Henkel Kommanditgesellschaft auf Aktien, Duesseldorf-Holthausen, Fed. Rep. of Germany

[21] Appl. No.: 534,592

[22] Filed: Jun. 6, 1990

[51] Int. Cl.⁵ ............................................. C07C 305/10
[52] U.S. Cl. ........................................ 558/34; 558/26
[58] Field of Search ...................................... 558/26, 34

[56] References Cited

U.S. PATENT DOCUMENTS 4,217,296  8/1980  Berkowitz .............................. 558/26
4,954,646  9/1990  Aigner et al. .......................... 558/34

Primary Examiner—Nicky Chan
Attorney, Agent, or Firm—Ernest G. Szoke; Wayne C. Jaeschke; Norvell E. Wisdom, Jr.

[57] ABSTRACT

Glycerol ether sulfates suitable for the production of manual dishwashing detergents and liquid and powdered laundry detergents are obtained by reaction of glycerol ethers in liquid phases with gaseous sulfur trioxide and subsequent neutralization with aqueous bases.

20 Claims, No Drawings

PROCESS FOR MAKING GLYCEROL ETHER SULFATES

FIELD OF THE INVENTION

This invention relates to a method for the preparation of glycerol ether sulfates by sulfatization of glycerol ethers and to the product glycerol ether sulfates. (As used herein, the term "glycerol ether sulfate" implies the presence of one monovalent cation, or a monovalent fraction of a higher valent cation, for each uncyclized sulfur atom in the molecule. The cation(s) are generally not included in the chemical names of the glycerol ether sulfates herein, except when needed to distinguish one material from another.) Glycerol ether sulfates are useful surfactants, and the use of the sulfates produced by a process according to this invention is also within the scope of the invention.

STATEMENT OF RELATED ART

It is known from DE-PS 757 749 and from JP-PS 82/44673 that glycerol ether sulfates can be used as auxiliaries in the textile and leather industry and for the production of dyes.

According to the German patent cited above (i.e., DE-PS 757 749), 1,3-glycerol dialkyl ethers can be converted into the secondary sulfates by reaction of the glycerol ethers with one of the following reagents: sulfuric acid, chlorosulfonic acid, amidosulfonic acid, adducts of pyridine with sulfur trioxide, and sulfur trioxide dissolved in an inert solvent, such as dimethylformamide, pyridine, or dichloroethane. However, all these reagents mentioned are attended by disadvantages from the industrial view point. Thus, the use of sulfuric acid as sulfonating agent results in an undesirably high electrolyte content in the products. Sulfatization with chlorosulfonic acid results unavoidably in the formation of highly corrosive hydrochloric acid, while the use of amidosulfonic acid allows only the production of glycerol ether sulfates including ammonium cations, rather than glycerol ether sulfates with cations other than ammonium. Adducts of pyridine with sulfur trioxide are difficult to handle and are unsuitable for use on an industrial scale. Finally, the use of sulfur trioxide dissolved in an inert solvent is attended by the problem that the solvent has to be separated from the product, and this separation requires considerable expenditure of energy. Avoiding any such need for separation of solvent is one object of this invention.

DESCRIPTION OF THE INVENTION

A major object of the present invention is to provide a process for making glycerol ether sulfates which does not have any of the disadvantages mentioned above.

Except in the operating examples, or where otherwise expressly indicated, all numerical quantities in this description indicating amounts of material or reaction conditions are to be understood as modified by the word "about" in defining the broadest scope of the invention. Practice of the invention within the boundaries corresponding to the exact quantities stated is preferable, however.

One embodiment of the present invention is a process for making glycerol ether sulfates, wherein sulfur trioxide in a gaseous phase is mixed with a liquid phase comprising, preferably initially consisting essentially of, one glycerol ether or a mixture of glycerol ethers corresponding to formula (I):

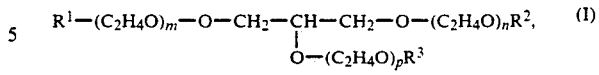

wherein $R^1$ is a $C_{4-22}$ alkyl radical; at least one of $R^2$ and $R^3$ is hydrogen and the other of $R^2$ and $R^3$ is hydrogen or a $C_{4-22}$ alkyl radical; and each of m, n, and p independently represents 0 or an integer in the range of 1 to 20 inclusive, subject to the constraint that the sum of $m+n+p$ is 0 or an integer within the range of 1 to 20 inclusive. The contacting is continued for a sufficient time to convert at least part of the glycerol ether content of the liquid phase that is contacted to an acidic sulfatization product. This acidic sulfatization product is then neutralized with some alkaline or basic material in aqueous solution to form the desired glycerol ether sulfate.

Glycerol ethers corresponding to formula (I) are known compounds and may be prepared by standard methods of preparative organic chemistry. Suitable processes for the production of glycerol ethers are, for example, the reactions of glycerine itself, or of adducts of an average of 1 to 20 moles of ethylene oxide and glycerine, with (i) alkyl halides (as described in DE-A-28 00 710) or (ii) olefin epoxides or butadiene and hydrogen in the presence of transition metal catalysts (as described in the *Journal of Molecular Catalysis*. 10, p. 247 (1981), and in *Oroanometallics* 5, 473, 514 (1986)).

Glycerol ether sulfates having particularly favorable performance properties are obtained when $R^1$ in formula (I) is a $C_8$ alkyl radical and $R^2$ is either the same as $R^1$ or represents hydrogen.

Glycerol ether sulfates distinguished by particularly advantageous dish washing and fabric cleaning power are derived from glycerol ethers corresponding to formula (I) in which m, n and p are 0.

Glycerol ether sulfates distinguished by particularly advantageous foaming power and high solubility in water are derived from glycerol ethers corresponding to formula (I) when the sum of m, n, and p is a number in the range from 2 to 10 inclusive.

The glycerol ether sulfates made by a process according to this invention have been observed, when dissolved in water, to produce solutions with less turbidity than corresponding solutions of glycerol ether sulfates made from the same starting glycerol ethers by prior art processes.

The reaction of the glycerol ether with gaseous sulfur trioxide may be carried out by methods known for use with fatty acid lower alkyl esters (as described by J. Falbe (ed.), *Surfactants in Consumer Products*, Springer Verlag, Berlin-Heidelberg, 1987, page 61), reactors of the falling-film type being preferred. The sulfur trioxide to be used in a process according to this invention is preferably diluted with an inert gas, more preferably selected from air and/or nitrogen, and is preferably contacted with the liquid containing the glycerol ether(s) to be sulfatized in the form of a gas mixture which contains the sulfur trioxide in a concentration of 1 to 8 % by volume and, more preferably, of 2 to 5 % by volume.

The molar ratio of the amount of glycerol ether(s) reacted to the content of sulfur trioxide contacted with the glycerol ether(s) by the completion of reaction in a process according to this invention is preferably in the range from 1:0.95 to 1:1.8, more preferably from 1:1.0 to 1:1.5. A process according to the invention is preferably carried out within the temperature range of 25 to 90° C. and more preferably within the temperature range of 35 to 80° C.

The products of reaction between sulfur trioxide and glycerol ethers are more acidic than is desirable for direct use as surfactants. Thus it is a part of a process according to this invention to mix these acidic sulfatization products, after completion of the sulfatization reaction, with aqueous solutions of bases, whereby the acid reaction products are neutralized and dissolved in the aqueous solution, which is preferably adjusted to a pH value in the range of 6.5 to 8.5. The neutralization is preferably carried out with bases selected from the group consisting of alkali metal hydroxides, such as sodium, potassium, and lithium hydroxide; alkaline earth metal oxides and hydroxides, such as magnesium oxide, magnesium hydroxide, calcium oxide, and calcium hydroxide; ammonia; mono-, di- and tri-$C_{2-4}$ alkanolamines, for example mono-, di- and triethanolamine; and primary, secondary or tertiary $C_{1-4}$ alkylamines. The bases used for neutralization are preferably used in the form of 5 to 55 % by weight aqueous solutions, 25 to 50 % by weight aqueous sodium hydroxide solution being most preferred.

After neutralization, the glycerol ether sulfate(s) obtainable by the process according to the invention are in aqueous solutions, normally including some unsulfatized glycerol ether(s) and inorganic sulfate(s) along with the glycerol ether sulfate, preferably having a solids content of 20 to 80 % by weight, more preferably of 30 to 50% by weight.

Where glycerol monoalkyl ethers are reacted with sulfur trioxide, mixtures of the corresponding primary and secondary monosulfates are obtained. In addition, the reaction mixture may contain disulfates and cyclic sulfuric acid esters. The products are light in color without bleaching, clear, and low in viscosity. If glycerol dialkyl ethers are used as starting materials for the sulfatization, secondary monosulfates are obtained in the form of light-colored, opaque, viscous pastes, even without bleaching.

After neutralization, the sulfatization products may be bleached in a known manner if desired, by addition of hydrogen peroxide or sodium hypochlorite solution to achieve a further lightening of color desirable for many applications. From 0.2 to 2 % by weight of pure hydrogen peroxide, or corresponding quantities of sodium hypochlorite, based on the solids content in the solution of the sulfatization products, is preferably used for this purpose.

The pH value of the solutions may be kept constant by using suitable buffers, for example sodium phosphate or citric acid. Also, addition of preservatives, for example formaldehyde solution, p-hydroxybenzoate, sorbic acid, or other known preservatives, is advisable for stabilization against bacterial contamination.

The glycerol ether sulfates obtainable by the process according to the invention show excellent detergent properties and are suitable for the production of surfactants, more particularly manual dishwashing detergents and liquid and powdered solid laundry detergents.

The following examples are intended to illustrate the invention without limiting it.

EXAMPLES

Preparation of the starting materials (not processes according to the invention)

A) 1-n-Octyl glycerol ether

An amount of 0.0038 gram ("g") 0.0125 millimole ("mmol") of palladium (II) acetyl acetonate, 0.0066 g =0.025 mmol of triphenyl phosphine, 28.8 g =313 mmol of glycerol, and 35 milliliters ("ml") of 2-propanol were introduced into a 400 ml glass autoclave equipped with a magnetic stirrer, evacuated a total of three times and placed under an argon atmosphere. An amount of 37.8 g =700 mmol of 1,3-butadiene was then transferred into the autoclave by means of a siphon. The autoclave was closed and kept for 12 hours at 70° C. After cooling and venting, a colorless liquid was obtained. This liquid was transferred into a 400 ml stainless steel autoclave equipped with a magnetic stirrer, and 0.5 % by weight, calculated on the total amount of starting materials, of Raney nickel was added to the autoclave contents. The gas space within the autoclave was filled with hydrogen, and the autoclave was then closed. The temperature of the autoclave contents was then raised to 180. C and maintained there for two hours, until the pressure within the autoclave fell to 1 atmo-sphere. The autoclave was then cooled and vented, and the liquid contents of the autoclave were separated from the catalyst to yield a colorless liquid having the following composition:

| | |
|---|---|
| 1-n-octyl glycerol ether | 34.0% by weight |
| 1,3- and 1,2-di-n-octyl glycerol ether | 21.7% by weight |
| 1,2,3-tri-n-octyl glycerol ether | 2.1% by weight |
| glycerol | 11.3% by weight |
| octane | 2.8% by weight |
| 2-propanol | 28.1% by weight |

This product was used for sulfatization without further purification.

B) 1,3- or 2,3-di-n-octyl glycerol ether

Example A) was repeated, except for using 10.3 g =112 mmol of glycerol, 13.5 g =250 mmol of 1,3-butadiene, and 1.0 g =13 mml of propane-1,2-diol instead of the 2-propanol. The reaction product (after hydrogenation) was obtained in the form of a light yellow colored liquid having the following composition:

| | |
|---|---|
| 1,3- and 1,2-di-n-octyl glycerol ether | 43.0% by weight |
| 1-n-octyl glycerol ether | 15.0% by weight |
| 1,2,3-tri-n-octyl glycerol ether | 17.8% by weight |
| propane-1,2-diol | 8.3% by weight |
| 1-n-octylpropane-1,2-diol ether | 5.1% by weight |
| 1,3-di-n-octylpropane-1,2-diol ether | 0.8% by weight |
| octane | 10.0% by weight |

The product was used for sulfatization without further purification.

$C_{12-14}$-alkyl glycerol 2EO ether

An amount of 180 g =1.00 mole ("mol") of an adduct of on average 2 mol ethylene oxide with each mol of glycerol was introduced into a 1 liter three-necked flask equipped with a stirrer, internal thermometer, and reflux condenser, followed by the addition of 218 g =2 mol of $C_{12-14}$ alkyl chloride and 112 g of potassium hydroxide flakes. The reaction mixture was then stirred for 5 hours at 110° C. After cooling, the basic reaction mixture was neutralized with hydrochloric acid and the excess alkyl chloride was distilled off. The yield of glycerol ethers was 95% of the theoretical quantity.

Preparation of glycerol ether sulfates according to the invention

EXAMPLES 1 to 4

In a 1 liter sulfatization reactor equipped with a jacket cooling system and a gas inlet, 1 mol of glycerol ether mixture prepared in Example A, B, or C was reacted with 0.95 to 1.2 mol of sulfur trioxide at a temperature of 35 or 80° C. The sulfur trioxide was driven off by heating from a corresponding quantity of 65% by weight oleum, diluted with nitrogen to a concentration of 5% by volume, and then introduced into the glycerol ether mixture over a period of 50 minutes. The crude sulfatization product was then neutralized with aqueous 25% by weight sodium hydroxide. The specific reaction conditions for each example and some characteristic data of the products are shown in Table 1.

APPLICATION EXAMPLES

Dish cleaning power

Cleaning power was evaluated by the so-called dish test as described in Fette, Seifen. Anstrichchemie, 74, 163 (1972). The test was carried out with water of either 3 or 16 degrees of German hardness ("·Gh") at 50° C., using 0.15 g of glycerol ether sulfate per liter water and beef tallow as soil. The tallow soil was used in a quantity of 2 g for each dish; the dishes were saucers about 14 centimeters in diameter, and the tallow was distributed over the central depression in the bottom of the saucers. The soiled dishes were washed under the described conditions after storage for 24 hours at room temperature. The results are shown in Table 2.

TABLE 1

REACTION CONDITIONS AND PRODUCT CHARACTERISTICS, EX. 1-4

| Ex. No. | Starting Mixture from Example: | Temperature. °C. | Molar Ratio of Ethers to SO$_3$ Reacted | Product Characterization, Wt. % | | | |
|---|---|---|---|---|---|---|---|
| | | | | WAS | UC | SO$_4^{-2}$ | H$_2$O |
| 1 | A | 35 | 1:1.20 | 38.1 | 3.8 | 0.7 | 57.4 |
| 2 | B | 35 | 1:1.20 | 30.3 | 17.0 | 0.2 | 52.5 |
| 3 | C | 80 | 1:0.95 | 26.2 | 6.5 | 0.4 | 66.9 |
| 4 | C | 80 | 1:1.03 | 37.6 | 7.6 | 0.6 | 54.2 |

Notes for Table 1

The anionic surfactant content ("WAS") and the unsulfatized components content ("UC") were determined in accordance with DGF Einheitsmethoden (Standard Methods), Stuttgart, 1950-1984, H-III-10 and G-II-6b. The SO$_4^{-2}$ content was expressed as sodium sulfate and the water content was determined by the Fischer method.

TABLE 2

| Glycerol ether sulfate of Ex. | Water hardness °Gh | Number of clean dishes |
|---|---|---|
| 2 | 3 | 11 |
| 2 | 16 | 5 |

Fabric washing power

Fabric washing power was tested in a Launderometer ™ using a mixed polyester and cotton, crease-resistant, fabric soiled with dust and sebum. The lightening of the washed fabric was determined by photometric reflectance measurements with an Elrepho ™ RFC-3/24 photometer against a barium sulfate standard of which the reflectance was put at 100%. The result is expressed in % reflectance ("% R"), with higher numbers indicating better washing power. The formulations for a phosphate-free powder detergent (formulation A) and a liquid detergent (formulation B) and also the washing conditions are shown below. The results of the washing tests are shown in Table 3.

| Formulation A: | |
|---|---|
| 8.0% by weight | Na glycerol ether sulfate of Example 1 or 2 |
| 4.0% by weight | Dehydol ® LT7, a Henkel product (adduct of, on average, 7 mol ethylene oxide with each mole of a technical mixed C$_{12-18}$ fatty alcohol) |
| 1.5% by weight | tallow soap, hydrogenated |
| 24.0% by weight | Sasil ® brand of zeolite A, a Henkel product |
| 10.0% by weight | sodium carbonate |
| 3.0% by weight | waterglass |
| 15.0% by weight | sodium perborate |
| 20.0% by weight | sodium sulfate |
| Formulation B: | |
| 13.0% by weight | Na glycerol ether sulfate, of Example 1 or 2 |
| 15.0% by weight | Dehydol ® LT7 |
| 13.0% by weight | coconut soap |
| 5.0% by weight | triethanolamine |
| 0.5% by weight | citric acid |
| Washing Conditions: | |
| Volume of wash liquor: | 250 ml |
| Weight ratio of fabric washed to water in the wash liquor: | 1:30 |
| Concentration of Formulation (A or B) in water used: | 10 grams/liter |
| Water hardness: | 16° Gh |

TABLE 3

| Glycerol ether sulfate of Example | Formulation A % R | Formulation B % R |
|---|---|---|
| 1 | 65.3 | 54.1 |
| 2 | 62.9 | 39.6 |

Notes for Table 3

Each value of % R shown is an average from 12 measurements.

What is claimed is:

1. A process for the production of glycerol either sulfates, wherein a gas phase containing sulfur trioxide is contacted at a temperature within the range from about 35 to about 80° C. with a liquid phase initially consisting essentially of one glycerol either or a mixture of glycerol ethers corresponding to formula (I):

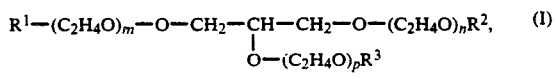

$$R^1-(C_2H_4O)_m-O-CH_2-CH-CH_2-O-(C_2H_4O)_nR^2, \quad (I)$$
$$| $$
$$O-(C_2H_4O)_pR^3$$

wherein $R^1$ is a C$_{4-22}$ aklyl radical; at least one of $R^2$ and $R^3$ is hydrogen and the other of $R^2$ and $R^3$ is hydrogen or a C$_{4-22}$ aklyl radical; and each of m, n, and p independently is zero or a positive integer and the sum of m + n + p is zero or an integer within the range of 1 to about 20 inclusive, for a sufficient time to convert at least part of said glycerol ether to an acidic sulfatization product, and said acidic sulfatization product is converted to a glycerol ether sulfate by neutralization by reaction with basic material dissolved in an aqueous solution.

2. A process as claimed in claim 1, wherein said glycerol either corresponds to formula (I) with $R^1$ and one of $R^2$ and $R^3$ each representing a $C_8$ alkyl radical.

3. A process as claimed in claim 1, wherein said glycerol either corresponds to formula (I) with $R^1$ representing a $C_8$ alkyl radical and each of $R^2$ and $R^3$ representing hydrogen.

4. A process as claimed in claim 1, wherein said glycerol either corresponds to formula (I) with each of m, n, and p having a value of 0.

5. A process as claimed in claim 1, wherein said glycerol either corresponds to formula (I) with the sum of m, n, and p being in the range from about 2 to about 10 inclusive.

6. A process as claimed in claim 5, characterized in that glycerol ether according to formula (I) and sulfur trioxide are used in a molar ratio of about 1:0.95 to about 1:1.8.

7. A process as claimed in claim 4, characterized in that glycerol ether according to formula (I) and sulfur trioxide are used in a molar ratio of about 1:0.95 to about 1:1.8.

8. A process as claimed in claim 1, characterized in that glycerol ether according to formula (I) and sulfur trioxide are used in a molar ratio of about 1:0.95 to about 1:1.8.

9. A process as claimed in claim 5, wherein said basic material dissolved in an aqueous solution is selected from the group consisting of alkali metal hydroxides, alkaline earth metal oxides and hydroxides, ammonia, mono-, di-, and tri-$C_{2-4}$ alkanolamines, and primary, secondary, and tertiary $C_{1-4}$ alkylamines.

10. A process as claimed in claim 4, wherein said basic material dissolved in an aqueous solution is selected from the group consisting of alkali metal hydroxides, alkaline earth metal oxides and hydroxides, ammonia, mono-, di-, and tri-$C_{2-4}$ alkanolamines, and primary, secondary, and tertiary $C_{1-4}$ alkylamines.

11. A process as claimed in claim 3, wherein said basic material dissolved in an aqueous solution is selected from the group consisting of alkali metal hydroxides, alkaline earth metal oxides and hydroxides, ammonia, mono-, di-, and tri-$C_{2-4}$ alkanolamines, and primary, secondary, and tertiary $C_{1-4}$ alkylamines.

12. A process as claimed in claim 2, wherein said basic material dissolved in an aqueous solution is selected from the group consisting of alkali metal hydroxides, alkaline earth metal oxides and hydroxides, ammonia, mono-, di-, and tri-$C_{2-4}$ alkanolamines, and primary, secondary, and tertiary $C_{1-04}$ alkylamines.

13. A process as claimed in claim 8, wherein said basic material dissolved in an aqueous solution is selected from the group consisting of alkali metal hydroxides, alkaline earth metal oxides and hydroxides, ammonia, mono-, di-, and tri-$C_{2-4}$-alkanolamines, and primary, secondary, and tertiary $C_{1-4}$ alkylamines.

14. A process as claimed in claim 7, wherein said basic material dissolved in an aqueous solution is selected from the group consisting of alkali metal hydroxides, alkaline earth metal oxides and hydroxides, ammonia, mono-, di-, and tri-$Cz_{2-4}$-alkanolamines, and primary, secondary, and tertiary $C_{1-4}$ alkylamines.

15. A process as claimed in claim 6, wherein said basic material dissolved in an aqueous solution is selected from the group consisting of alkali metal hydroxides, alkaline earth metal oxides and hydroxides, ammonia, mono-, di-, and tri-$C_{2-4}$-alkanolamines, and primary, secondary, and tertiary $C_{1-4}$ alkylamines.

16. A process as claimed in claim 1, wherein said basic material dissolved in an aqueous solution is selected from the group consisting of alkali metal hydroxides, alkaline earth metal oxides and hydroxides, ammonia, mono-, di-, and tri-$C_{2-4}$-alkanolamines, and primary, secondary, and tertiary $C_{1-4}$ alkylamines.

17. A process as claimed in claim 3, characterized in that glycerol either according to formula (I) and sulfur trioxide are used in a molar ratio of about 1:0.95 to about 1:1.8.

18. A process as claimed in claim 2, characterized in that glycerol ether according to formula (I) and sulfur trioxide are used in a molar ratio of about 1:0.95 to about 1:1.8.

19. A process as claimed in claim 18, wherein said basic material dissolved in an aqueous solution is selected from the group consisting of alkali metal hydroxides, alkaline earth metal oxides and hydroxides, ammonia, mono-, di-, and tri-$C_{2-4}$-alkanolamines, and primary, secondary, and tertiary $C_{1-4}$ alkylamines.

20. A process as claimed in claim 17, wherein said basic material dissolved in an aqueous solution is selected from the group consisting of alkali metal hydroxides, alkaline earth metal oxides and hydroxides, ammonia, mono-, di-, and tri-$C_{2-04}$-alkanolamines, and primary, secondary, and tertiary $C_{1-4}$ alkylamines.

* * * * *

UNITED STATES PATENT AND TRADEMARK OFFICE
CERTIFICATE OF CORRECTION

PATENT NO. : 5,117,032
DATED : May 26, 1992
INVENTOR(S) : Fabry et al.

It is certified that error appears in the above-identified patent and that said Letters Patent is hereby corrected as shown below:

In claim 7, column 7, line 27, the word "either" should read --ether--.

In claim 8, column 7, line 31, the word "either" should read --ether--.

In claim 12, column 8, line 6, "$C_{1O4}$" should read --$C_{1-4}$--.

In claim 14, column 8, line 17, "$C_{z\ 2-4}$" should read --$C_{2-4}$--.

In claim 17, column 8, line 32, the word "either" should read --ether--.

In claim 20, column 8, line 49, "$C_{2O4}$" should read --$C_{2-4}$--.

Signed and Sealed this

Seventeenth Day of August, 1993

Attest:

BRUCE LEHMAN

*Attesting Officer*           *Commissioner of Patents and Trademarks*